United States Patent
Bulut et al.

(10) Patent No.: US 11,540,780 B2
(45) Date of Patent: Jan. 3, 2023

(54) DEVICE, SYSTEM AND METHOD FOR DETERMINING A VITAL SIGN OF A PERSON

(71) Applicant: KONINKLIJKE PHILIPS N.V., Eindhoven (NL)

(72) Inventors: Murtaza Bulut, Eindhoven (NL); Albertus Cornelis Den Brinker, Eindhoven (NL); Gerrit Maria Kersten, Veldhoven (NL); Michel Jozef Agnes Asselman, Nuenen (NL)

(73) Assignee: Koninklijke Philips N.V., Eindhoven (NL)

( * ) Notice: Subject to any disclaimer, the term of this patent is extended or adjusted under 35 U.S.C. 154(b) by 769 days.

(21) Appl. No.: 16/063,345

(22) PCT Filed: Dec. 15, 2016

(86) PCT No.: PCT/EP2016/081097
§ 371 (c)(1),
(2) Date: Jun. 18, 2018

(87) PCT Pub. No.: WO2017/108548
PCT Pub. Date: Jun. 29, 2017

(65) Prior Publication Data
US 2018/0360387 A1   Dec. 20, 2018

(30) Foreign Application Priority Data
Dec. 23, 2015 (EP) .................................. 15202270

(51) Int. Cl.
*A61B 5/00* (2006.01)
*A61B 5/18* (2006.01)
(Continued)

(52) U.S. Cl.
CPC .......... *A61B 5/7221* (2013.01); *A61B 5/0205* (2013.01); *A61B 5/02416* (2013.01);
(Continued)

(58) Field of Classification Search
CPC ..... A61B 5/6801; A61B 5/683; A61B 5/6893; A61B 5/6886; A61B 5/7221
See application file for complete search history.

(56) References Cited

U.S. PATENT DOCUMENTS 8,525,679 B2 *  9/2013  Riley .................. A61B 5/6892
                                                        5/607
9,943,371 B2 *  4/2018  Bresch ................ A61B 5/0077
(Continued)

FOREIGN PATENT DOCUMENTS

CN   103978977 A   8/2014
EP    2898825 A1   7/2015
(Continued)

OTHER PUBLICATIONS

Verkruysse et al., "Remove plethysmographic imaging using ambient light", Optics Express, 16(26), Dec. 22, 2008, pp. 21434-21445.
(Continued)

*Primary Examiner* — Eric D. Bertram

(57) ABSTRACT

The present invention relates to a device, system and method for determining a vital sign of a person. To improve accuracy and reliability of vital sign determination, the device comprises an input unit (20) for obtaining a vital sign related signal of at least a body part of the person, from which a vital sign can be derived, a body part position determining unit (21) for determining if said body part of the person is in contact with a support or not and generating a contact signal indicating if said body part is in contact with the support or not, a quality metric setting unit (22) for setting, based on said contact signal, a quality metric for use in the determi-
(Continued)

nation of a vital sign of the person, and a vital sign deriving unit (23) for deriving a vital sign from the obtained vital sign related signal, wherein the set quality metric is used in the derivation of the vital sign and/or in a judgment of the reliability of a derived vital.

30 Claims, 5 Drawing Sheets

(51) Int. Cl.
  *A61B 5/024* (2006.01)
  *G06T 7/70* (2017.01)
  *A61B 5/0205* (2006.01)
  *G06T 7/20* (2017.01)
  *A61B 5/08* (2006.01)
  *A61B 5/11* (2006.01)

(52) U.S. Cl.
  CPC .............. *A61B 5/18* (2013.01); *A61B 5/486* (2013.01); *A61B 5/6801* (2013.01); *A61B 5/6886* (2013.01); *A61B 5/6893* (2013.01); *A61B 5/7278* (2013.01); *G06T 7/20* (2013.01); *G06T 7/70* (2017.01); *A61B 5/0077* (2013.01); *A61B 5/02427* (2013.01); *A61B 5/0816* (2013.01); *A61B 5/1114* (2013.01); *A61B 5/1128* (2013.01)

(56) References Cited

U.S. PATENT DOCUMENTS

| | | | |
|---|---|---|---|
| 2004/0138580 A1* | 7/2004 | Frei | A61B 5/04012 600/544 |
| 2008/0288143 A1 | 11/2008 | Smith et al. | |
| 2008/0294017 A1 | 11/2008 | Gobeyn et al. | |
| 2009/0306484 A1 | 12/2009 | Kurtz et al. | |
| 2014/0039330 A1* | 2/2014 | Seo | A61B 5/6893 600/509 |
| 2014/0058263 A1 | 2/2014 | Baym et al. | |
| 2014/0066795 A1* | 3/2014 | Ferdosi | A61B 5/0428 600/509 |
| 2014/0253709 A1 | 9/2014 | Bresch et al. | |
| 2014/0276099 A1 | 9/2014 | Kirenko et al. | |
| 2014/0285216 A1* | 9/2014 | Cuddihy | B60N 2/002 324/658 |
| 2015/0173631 A1* | 6/2015 | Richards | A61B 5/02427 600/479 |
| 2017/0000347 A1 | 1/2017 | Meftah et al. | |

FOREIGN PATENT DOCUMENTS

| | | |
|---|---|---|
| WO | 2014128273 A1 | 8/2014 |
| WO | 2015055405 A1 | 4/2015 |

OTHER PUBLICATIONS

Kuo J., Koppel S., Charlton J.L., Rudin-Brown, C.M., "Evaluation of a video-based measure of driver heart rate", Journal of Safety Research, 2015.

"Head Restraints and Whiplash", The Royal Society for the Prevention of Accidents, https://www.rospa.com/road-safety/advice/vehicles/head-restraints-and-whiplash/, accessed Jun. 18, 2018.

"Head restraint", https://en.wikipedia.org/wiki/Head_restraint, accessed Jun. 18, 2018, last edited Dec. 2017.

Jeanne, V. et al., "Camera-based heart rate monitoring in highly dynamic light conditions", 2013, International Conference on Connected Vehicles and Expo, The Netherlands, pp. 798-799.

* cited by examiner

DEVICE, SYSTEM AND METHOD FOR DETERMINING A VITAL SIGN OF A PERSON

CROSS-REFERENCE TO PRIOR APPLICATIONS

This application is the U.S. National Phase application under 35 U.S.C. § 371 of International Application No. PCT/EP2016/081097 filed on 15 Dec. 2016, which claims the benefit of European Patent Application No. 15202270.3, filed on 23 Dec. 2015. These applications are hereby incorporated by reference herein.

FIELD OF THE INVENTION

The present invention relates to a device, system and method for determining a vital sign of a person, in particular of a person being at least partly and temporarily in contact with a support (also called stationary object), such as a seat, table, chair, bed, couch, etc.

BACKGROUND OF THE INVENTION

Vital signs of a person, for example the heart rate (HR), the respiration rate (RR) or the arterial blood oxygen saturation (SpO2), serve as indicators of the current health state of a person and as powerful predictors of serious medical events. For this reason, vital signs are extensively monitored in inpatient and outpatient care settings, at home or in further health, leisure and fitness settings. However, also in other scenarios acquisition of vital signs is useful, e.g. to monitor the health state of a driver in a vehicle (e.g. a car, truck, train, ship, airplane, helicopter, etc.). In such scenarios the person is usually sitting in a seat having a head-rest.

One way of measuring vital signs is plethysmography. Plethysmography generally refers to the measurement of volume changes of an organ or a body part and in particular to the detection of volume changes due to a cardio-vascular pulse wave traveling through the body of a subject with every heartbeat.

Photoplethysmography (PPG) is an optical measurement technique that evaluates a time-variant change of light reflectance or transmission of an area or volume of interest. PPG is based on the principle that blood absorbs light more than surrounding tissue, so variations in blood volume with every heart beat affect transmission or reflectance correspondingly. Besides information about the heart rate, a PPG waveform can comprise information attributable to further physiological phenomena such as the respiration. By evaluating the transmittance and/or reflectivity at different wavelengths (typically red and infrared), the blood oxygen saturation (SpO2) can be determined. Different kinds of such contact sensors (also called wearable devices) are commonly known and used, including contact finger pulse oximeters, contact forehead pulse oximeter sensors, contact pulse sensors, etc.

Recently, non-contact, remote photoplethysmography (rPPG) devices (also called camera-based PPG devices) for unobtrusive measurements have been described in many publications, e.g. in Verkruysse et al., "Remote plethysmographic imaging using ambient light", Optics Express, 16(26), 22 Dec. 2008, pp. 21434-21445, which demonstrates that photoplethysmographic signals can be measured remotely using ambient light and a conventional consumer level video camera, using red, green and blue color channels.

Remote PPG utilizes light sources or, in general radiation sources, arranged remotely from the subject of interest. Similarly, also a detector, e.g., a camera or a photo detector, can be arranged remotely from the subject of interest, i.e. without contact to the subject. Therefore, remote photoplethysmographic systems and devices are considered unobtrusive and well suited for medical as well as non-medical everyday applications.

Using unobtrusive systems like camera based systems, another way of measuring vital signs is by measuring the motion of chest and head to determine respiration and heart rate, respectively.

Further, another way of measuring vital signs is by using wearable sensors for measuring the respiration and heart rate from movement of the body part to which the sensor is attached to, such as chest, arm, head, etc., or by using conventional PPG in an optical contact sensor.

However, for practical application like e.g. a car environment, the SNR (signal to noise ration) is not at a level that a sufficiently high quality vital sign calculation can be guaranteed. In general, remote PPG systems will produce an output at all times, which can result in vital sign values which are wrong and meaningless, for instance when the person (e.g. the driver of a car) is moving a lot and/or when there are undesirable lighting conditions. Is it possible to only provide an output when the signal meets certain criteria e.g. sufficient applitude but this can result in periods of no output. It is desirable to produce a reliable output.

SUMMARY OF THE INVENTION

It is an object of the present invention to provide a device, system and method for reliably and accurately determining a vital sign of a person.

In a first aspect of the present invention a device for determining a vital sign of a person is presented, said device comprising
  an input unit for obtaining a vital sign related signal of at least a body part of the person, from which a vital sign can be derived,
  a position determining unit for determining if said body part of the person is in contact with a support or not and generating a contact signal indicating if said body part is in contact with the support or not,
  a quality metric setting unit for setting, based on said contact signal, a quality metric for use in the determination of a vital sign of the person, and
  a vital sign deriving unit for deriving a vital sign from the obtained vital sign related signal, wherein the set quality metric is used in the derivation of the vital sign and/or in a judgment of the reliability of a derived vital.

In a further aspect of the present invention a system for determining a vital sign of a person is presented, said system comprising
  a vital sign related signal acquisition unit for acquiring a vital sign related signal of at least a body part of the person, from which a vital sign can be derived, and
  a device as disclosed herein for determining a vital sign of the person based on the acquired vital sign related signal.

When applied to the quality metric, the terms "setting" and "calculating" may be understood as being the same.

In yet further aspects of the present invention, there are provided a corresponding method, a computer program which comprises program code means for causing a computer to perform the steps of the method disclosed herein when said computer program is carried out on a computer as well as a non-transitory computer-readable recording medium that stores therein a computer program product, which, when executed by a processor, causes the method disclosed herein to be performed.

Preferred embodiments of the invention are defined in the dependent claims. It shall be understood that the claimed methods, processor, computer program and medium have similar and/or identical preferred embodiments as the claimed device and system, in particular as defined in the dependent claims and as disclosed herein.

The present invention is based on the idea to consider and measure those (external) condition(s) which, to a large degree, ensure that a reliable vital sign estimate can be obtained by the device, system and method. It has particularly been found that certain cases, in particular when at least a body part of the person, from which vital signs shall be derived, is at least temporarily in contact with a support (e.g. if the person's head is resting on a head-rest of a seat), are favorable over the others.

For instance, driving when the head is resting on the head-rest is not uncommon for highway driving. It could be expected that with the introduction of autonomous vehicles, in most cases, for most drivers the head may rest on the head-rest. Also, when waiting at traffic lights, many drivers rest their head on the head-rest. Further, many passengers rest their head on the head-rest. For vital signs determination or monitoring in the car, the main factor that affects performance is motion of the person whose vital signs shall be determined or monitored, in particular the head motion. However, when the head of the driver is resting on the head-rest (at least for a certain duration required for acquiring the respective vital sign), the person's vital sign(s) can be determined with high reliability.

Recognition of this situation, is generally evaluated, according to the present invention, by using a quality metric (sometimes also called confidence metric or reliability metric or quality metric parameter) that takes into account if the person's body part, from which vital sign(s) shall be acquired, such as the head of a person if the heart rate shall be derived from video data of the person's face, is resting on a support or not. Optionally, as provided according to preferred embodiments other factors may be used in addition.

Thus, according to the present invention it is detected when the person's body part is in contact with the support, and the quality metric is set (or obtained), e.g. by changing one or more metric parameters or by making use of past vital sign values determined earlier while the body part was also in contact with the support. In this way, vital signs of a person, e.g. sitting in a chair having a head-rest or sitting or lying on a bed or couch, can be determined more accurately and reliably.

There are generally a number of different options available for use of the quality metric. In particular, based on the quality metric, another way of processing may be chosen, and/or an indicator of reliability may be issued to the person (or another user, like a nurse or care giver), and/or it may be decided not to present the derived vital sign to the person (because it is considered unreliable). If, in the latter case, it is decided to present a previous value of the vital sign (that was considered reliable) this may be considered as a kind of modification of the processing.

The present invention may process different kinds of vital sign related signals obtained (i.e. retrieved or received) by the input unit as input. In one embodiment a temporal sequence of images of at least one body part of the person acquired by an imaging unit is obtained as one ore more vital sign related signals. Such an imaging unit may e.g. be a camera, such as an RGB camera, video camera, web cam, etc., which e.g. records video data as a temporal sequence of images (also called image frames). In another embodiment one or more wearable sensor signal(s) of said at least one body part of the person is obtained as one or more vital sign related signals. Such wearable sensor signals are acquired by one or more wearable sensor, such as a heart rate sensor, a respiration sensor, an SpO2 sensor, an accelerometer, a motion sensor, or any other sensor that can be worn at the person's body to record a wearable sensor signal, from which a vital sign of the person can be derived or which directly represents a vital sign. For instance, a conventional optical contact sensor (e.g. comprising two LEDs and one photodiode) may be used as wearable sensor, by which a spot on the subject's skin is irradiated by radiation (particularly at two different wavelength ranges) and radiation transmitted through and/or reflected by the irradiated skin and the underlying tissue is received forming said at least one vital sign related signal.

An exemplary processing works as follows: for every image frame (of a temporal sequence of image frames obtained as vital signs related signal) an output value (i.e. a vital sign value) is generated. Afterwards, the check is performed (based on the quality metric) whether to accept or reject this output. Thus, two quality metrics may be used in this implementation, one for the situation when contact of the body part with the support is detected and one for the situation when the body part is free. In the former case, the quality metric will be relaxed, because it has been observed (and therefore expected) that most of the outputs (when the body part is resting) are correct.

According to a preferred embodiment said quality metric setting unit is configured to additionally use, for setting the quality metric, one or more of the illumination level, light intensity variations, motion of the person, motion of the body part, motion of the support, motion of the body part relative to the support, kind and/or parameter of an algorithm for vital sign derivation. This further improves the accuracy and reliability of the vital sign determination.

There are different options to determine if the person's body part is in contact with the support. In one embodiment said body part position determining unit is configured to determine if said body part of the person is in contact with the support or not by analyzing the obtained sequence of images representing said vital sign related signal. Particularly, the position, movement and/or orientation of the body part with respect to the support in the obtained sequence of images may be detected for this purpose by image processing means. For instance, a known algorithm using e.g. pattern detection or feature detection may be applied to detect the relative position of the body part with respect to the support.

In another embodiment said body part position determining unit is configured to receive a detection signal from an object sensor in or at the support configured to detect contact of a person's body part with the support and for generating said contact signal from said detection signal. Said object sensor may e.g. an optical sensor, a capacitive sensor, a mechanical sensor, a pressure sensor, a motion sensor, etc., which is embedded into the support or mounted on its outer surface.

In another embodiment, said body part position determining unit is configured to analyze the obtained vital sign related signal to determine if the body part from which the signal is extracted has been in contact with a support or not. This can be done by calculating the signal to noise ratio, since for signal acquired when the body part is supported, the signal to noise ratio will be greater than a predetermined threshold. In addition, the acquired signal can be checked if it satisfies certain conditions, which are inspired by the expected physiological changes, such as having certain amplitude or frequency ranges or variations. Moreover, data mining approach can be also followed, by collecting representative data for conditions with and without support, and using these data to train and test models to determine if the body part is in contact with the support or not.

Preferably, said vital sign deriving unit may be configured to label vital signs derived when said body part of the person is determined to be in contact with the support as reliable. Generally, it is assumed that the person's body part is moved less (i.e., it has fewer degrees of freedom) if it is in contact with a support (at least for a minimum duration) so that the reliability of vital signs acquired under such conditions is generally considered to be higher than in case the person's body part is not contact with the support.

Vital signs labeled as reliable can then be used for judging the reliability of subsequently acquired vital signs, in particular if and/or to which extent an acquired vital sign is reliable. For instance, in an embodiment said vital sign deriving unit is configured to determine if a vital sign derived within a predetermined time period after a vital sign labeled as reliable has been derived deviates from said vital sign by more than a predetermined percentage and to label vital signs deviating by less than said predetermined percentage as reliable. A corresponding user information may be issued, e.g. like an indicator light showing a green light if the estimated vital sign can be trusted and a red light if it is a questionable measurement result.

The device may further comprise an support control unit for generating an support control signal for controlling the position of the support to get in contact with said body part of the person if it has been determined that said body part of the person is not in contact with the support and a vital sign of the person shall be determined. This will make sure that the acquired vital signs will then be more reliable and accurate.

The device may further comprise a user instruction generator for generating a user instruction instructing the person to move said body part to get in contract with the support if it has been determined that said body part of the person is not in contact with the support and a vital sign of the person shall be determined. If the person follows the instruction, this will also make sure that the acquired vital signs will then be more reliable and accurate.

In another embodiment said quality metric setting unit is configured to additionally use the lighting conditions in the setting of the quality metric. It has e.g. been found that during night time the reliability of acquired vital signs is increased, which will thus be taken into account in this embodiment.

Depending on the kind of scenario and application different supports and different body parts may be considered. Hence, in an embodiment said input unit is configured to obtain a temporal sequence of images of at least the person's face, hand, arm, torso, leg, or foot and wherein said position determining unit is configured to determine if the person's head is in contact with a headrest, the person's arm and/or hand is in contact with a arm-rest, the person's torso is in contact with a back-rest, the person's leg is in contact with a seating or lying area and/or the person's foot is in contact with a footrest.

In addition to the imaging unit and the disclosed device, the disclosed system may further comprise an object sensor arranged in or at a support for detecting contact of said body part of the person with the support and for generating a detection signal indicating if said body part of the person is in contact with the support. Further, an actuator for adjusting the position of the support to get in contact with said body part of the person based on a support control signal and/or a user interface for issuing a user instruction instructing the person to move said body part to get in contract with the support may be provided.

The vital sign related signal acquisition unit of the disclosed system may comprise an imaging unit and/or one or more wearable sensors.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Figure 1A:
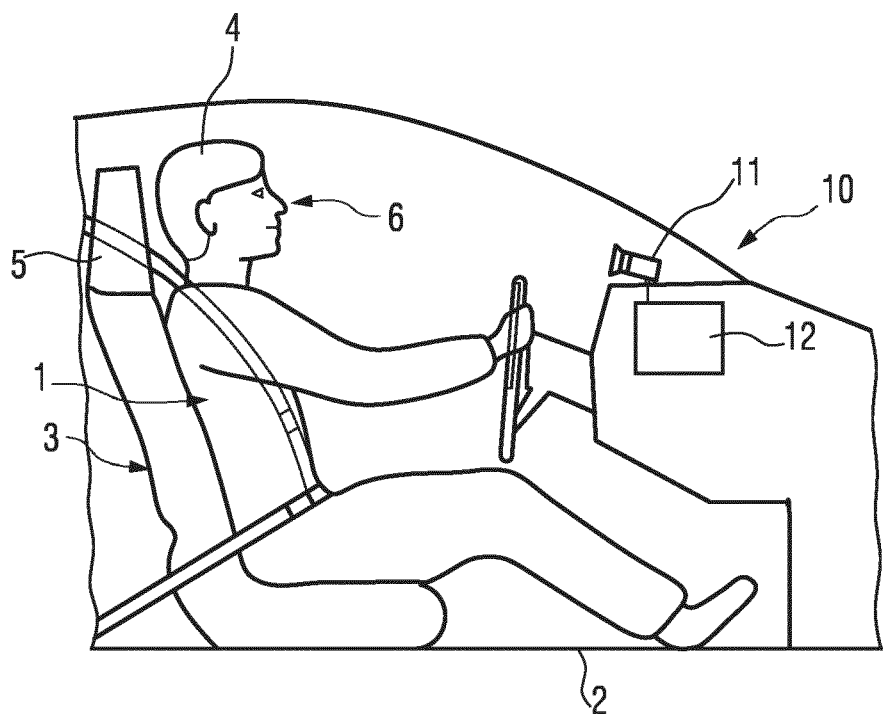
FIG. 1 shows a diagram illustrating a system according to the present invention in an exemplary use scenario.
Figure 1B:
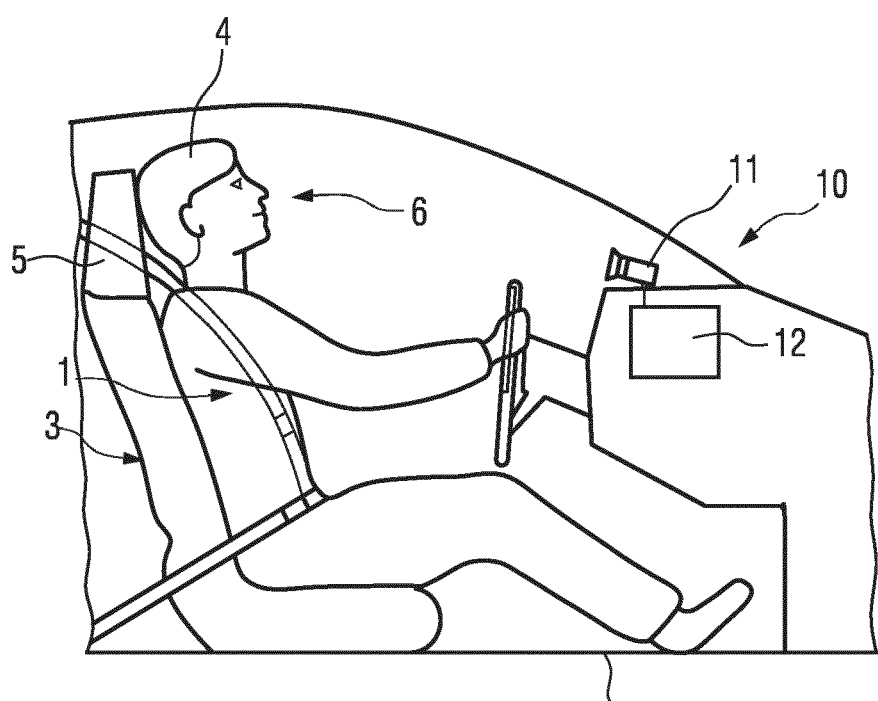

FIG. 1 shows a diagram illustrating an exemplary use scenario of the system according to the present invention. In this use scenario the device, system and method of the present invention are used to determine a vital sign, in particular the heart rate and/or respiration rate, of a person (driver) 1 driving a car 2. For acquiring a vital sign related signal an imaging unit 11 is preferably used as exemplary embodiment of the vital sign related signal acquisition unit, which imaging unit 11 acquires a temporal sequence of images. In other embodiments, one or more wearable sensors may be additionally or alternatively used to acquire a vital sign related signal, While driving, during some time periods the driver 1 will sit in the seat 3 at two main different positions, namely with his head 4 being not in contact with the head-rest 5, as shown in FIG. 1A, or with his head 4 being in contact with the head-rest 5, as shown in FIG. 1B.

The system 10 according to the present invention comprises an imaging unit 11 for acquiring a temporal sequence of images of at least a body part (in this exemplary use scenario of the face 6, i.e. a skin area) of the person 1. From these images of the face vital signs of the person 1 can be derived by use of the known principle of remote photoplethysmography (remote PPG). This is performed by the device 12 according to the present invention as will be explained in more detail below.

The imaging unit 11 may be a camera (also referred to as camera-based or remote PPG sensor) including a suitable photosensor for (remotely and unobtrusively) capturing image frames of the person 1 (at least of the face 6 in this exemplary use scenario), in particular for acquiring a sequence of image frames over time, from which photoplethysmography signals can be derived. The image frames captured by the camera may particularly correspond to a video sequence captured by means of an analog or digital photosensor, e.g. in a (digital) camera. Such a camera usually includes a photosensor, such as a CMOS or CCD sensor, which may also operate in a specific spectral range (visible, IR) or provide information for different spectral ranges. The camera may provide an analog or digital signal. The image frames include a plurality of image pixels having associated pixel values. Particularly, the image frames include pixels representing light intensity values captured with different photosensitive elements of a photosensor. These photosensitive elements may be sensitive in a specific spectral range (i.e. representing a specific color). The image frames include at least some image pixels being representative of a skin portion of the subject. Thereby, an image pixel may correspond to one photosensitive element of a photo-detector and its (analog or digital) output or may be determined based on a combination (e.g. through binning) of a plurality of the photosensitive elements.

Figure 2:
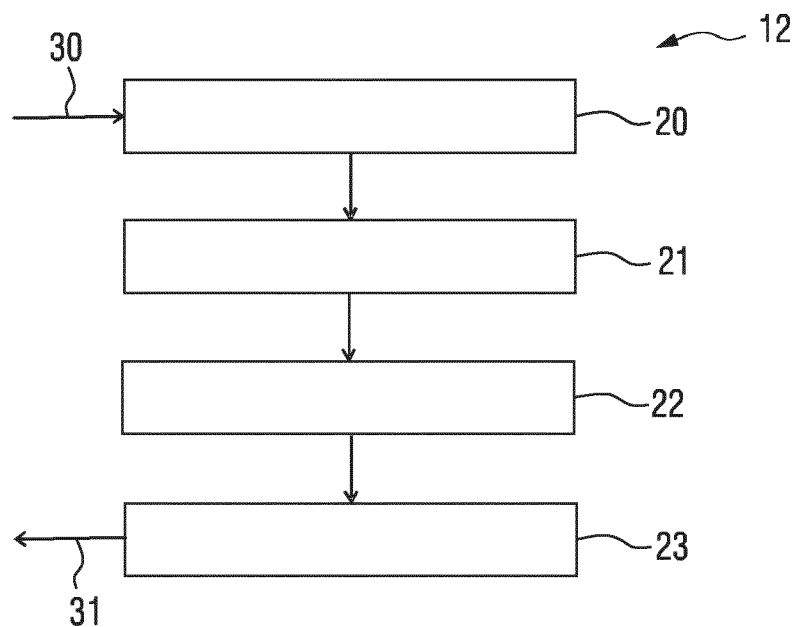
FIG. 2 shows a schematic diagram of a first embodiment of device according to the present invention.

FIG. 2 shows a schematic diagram of a first embodiment of device 12 according to the present invention. The device 12 comprises an input unit 20 for obtaining (e.g. receiving or retrieving) a temporal sequence of images 30 of at least a body part (in the use scenario of FIG. 1 at least the face 6) of the person 1, from which a vital sign can be derived. The images are generally acquired and provided on the fly by the imaging unit 11, but may also be buffered if needed before they are provided to and/or processed by the device 12. The input unit 20 may e.g. be configured as a data interface, e.g. a serial interface, a parallel interface, a HDMI interface or any other suitable interface.

The device 12 further comprises a body part position determining unit 21 for determining if said body part (i.e. the head 4 of the person 1 is in contact with a support (in the use scenario of FIG. 1 the head-rest 5) or not and generating a contact signal indicating if said body part is in contact with the support or not. Daytime and night time highway driving data (driving speed varying between 60-130 km/h), which includes more than 10 hours of driving and 6 drivers of heart rates ranging from 60 to 90 have shown that when the head is resting on the head-rest, the heart rate can be calculated with high accuracy and reliability.

A quality metric setting unit 22 is provided for setting, based on said contact signal, a quality metric for use in the determination of a vital sign of the person. A vital sign deriving unit 23 is provided for deriving a vital sign 31 from the obtained sequence of images, in particular by use of remote PPG, wherein the set quality metric is used in the derivation of the vital sign and/or in a judgment of the reliability of a derived vital.

One or more of the units of the device 12 may be comprised in one or multiple digital or analog processors depending on how and where the invention is applied. The different units may completely or partly be implemented in software and carried out on a computer connected to one or more detectors. Some or all of the required functionality may also be implemented in hardware, e.g. in an application specific integrated circuit (ASIC) or in a field programmable gate array (FPGA).

The detection of whether the person's body part (in the exemplary use scenario, the driver's head 4) is resting on the head-rest 5 can be done in different ways. In one embodiment, the body part position determining unit 21 is configured to determine if said body part of the person is in contact with the support or not by analyzing the obtained sequence of images 30. Particularly the position, movement and/or orientation of said body part with respect to the support are detected in the obtained sequence of images. For instance, the head 6 is detected and head motion and head position are analyzed within the sequence of images 30. Detecting that the head position does not change and that head movements are limited and similar to torso movements are used as indicators to determine if the head 6 is resting on the head-rest 5 or not.

Figure 3:
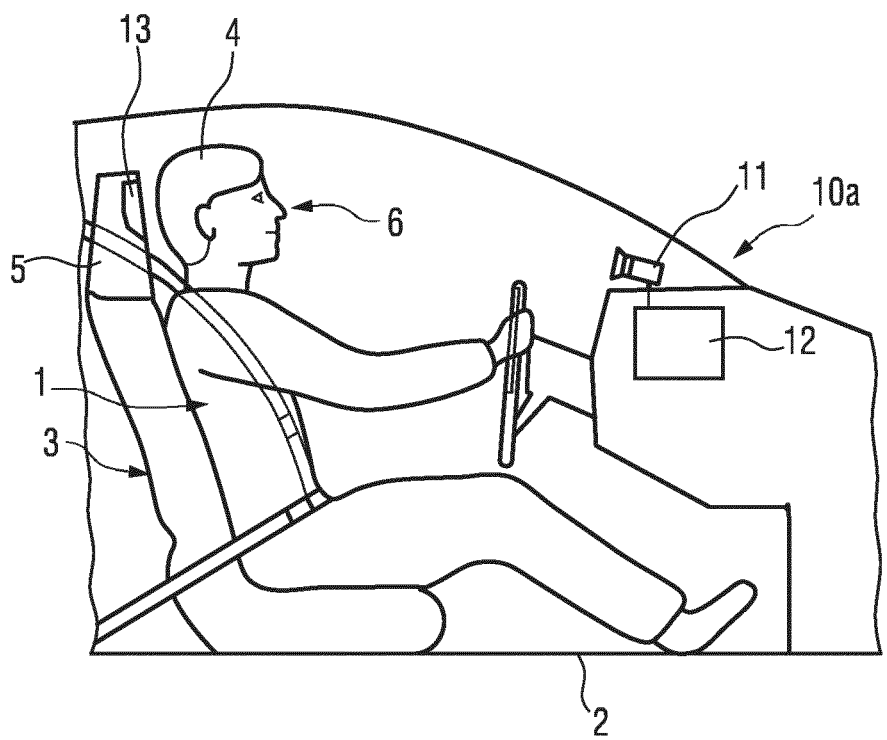
FIG. 3 shows a schematic diagram of a second embodiment of a system according to the present invention.

In another embodiment the body part position determining unit 21 is configured to receive a detection signal from an object sensor 13 in or at the support configured to detect contact of a person's body part with the support and for generating said contact signal from said detection signal. This is illustrated in FIG. 3 showing another embodiment of the proposed system 10a in the exemplary use scenario illustrated in FIG. 1. In this embodiment the system 10a further comprises an object sensor 13 arranged in or at the head-rest 5 for detecting contact of the person's head 4 with the head-rest 5 and for generating a detection signal indicating if the person's head 4 is in contact with the head-rest 5. This detection signal is then provided to the device 12 (e.g. in a wired or wireless manner, e.g. via the on-board network of the car 2) for use by the body part position determining unit 21 as explained above. For instance, the object sensor 13 may be or include an optical sensor, a capacitive sensor, a mechanical sensor, a pressure sensor, etc. In a further embodiment, the object sensor 13 may be or include a motion sensor (e.g. an inertial sensor). When the body part is in contact with the support, the motion sensor can provide additional information on the motion of the body part compared to the sensor (and thus the confidence of the vital sign that is being measured).

In an implementation of the proposed idea in the exemplary use scenario, when contact of the head with the head-rest is detected (i.e. when it is detected that the head of the driver is resting on the head-rest), the default quality metric calculation parameters can be relaxed (e.g. a first quality metric is used). For this case, relaxing the quality metric requirements will increase the sensitivity of the system, without decreasing the accuracy. This can be done, for example, by increasing the range of acceptable signal amplitude values. By doing so, the percentage of time the proposed device 12 produces a vital sign output (that is, the sensitivity of the device) can be increased. By relaxing the quality metric calculation parameters (for example acceptable signal amplitude), the device 12 can produce a reliable vital sign more often without sacrificing on the vital sign quality because it is assumed that even without the strict quality metric in head-rest condition the vital signs are accurate.

In contrast, when it is detected that the head is not supported by the support (i.e., headrest) anymore, the requirements on the quality metric can be more demanding (e.g. a second "stricter" quality metric is used) to ensure that all type of noise and artifacts resulting from the increased degrees of freedom of head can be filtered. Having stricter requirements can mean that sensitivity of system is decreases (i.e., output is produced fewer times in comparison to the relaxed quality metric condition) in order to ensure that calculated output values are accurate.

Thus, in general, at least two quality metrics may be applied i.e. used. It is, however, possible to use further quality metrics in further situations. For example, in city driving conditions, where the driver's motion is expected to be greater, a third quality metric may be employed.

In another implementation of the proposed idea, when contact of the head with the head-rest is detected, the desired vital sign (e.g. heart rate) is calculated using the stricter (i.e., more demanding, second) quality metric. Hence, by using both the demanding (second) quality metric and the information that the head is on the head-rest the confidence that the measured vital signal values are accurate is increased. The calculated vital sign values are then stored (e.g. in a memory of the device, not shown) and labeled as "true" (or "reliable"), i.e. it is assumed that they are correct.

For the next time period (e.g. in the range of 15-45 min, e.g. 30 min, or another user-defined time period) from the last time a "reliable" vital sign has been calculated, a vital sign band is defined based on the last detected "reliable" values. If new calculated values are outside this band, they are likely to be incorrect and considered as "unreliable". The band can e.g. be defined by using the reliable value ±X % (X being e.g. in the range of 5-25, e.g. 10 or 20) or ±Y (Y being an absolute number reflecting a certain percentage; e.g. Y being in the range from 5-15 BPM (beats per minute), e.g. 10 BPM, for heart rate values). Heart rate changes during driving do generally not happen very quickly, but only happen gradually over a longer period of time, so a period of e.g. 30 min may be a good choice for the time period, if there are no unexpected changes in the driving conditions.

If the newly calculated vital sign values are inside the band they are likely to be correct ("reliable") even if they do not meet the strict quality metric conditions (because the quality metric was designed to have high specificity, which naturally results in lower sensitivity). In this case, the vital sign values can be issued, e.g. to the driver or another user. The benefit of this implementation is that the sensitivity of the device (i.e. the percentage of times an accurate vital sign value is shown) can be increased without compromising on the quality.

Figure 4A:
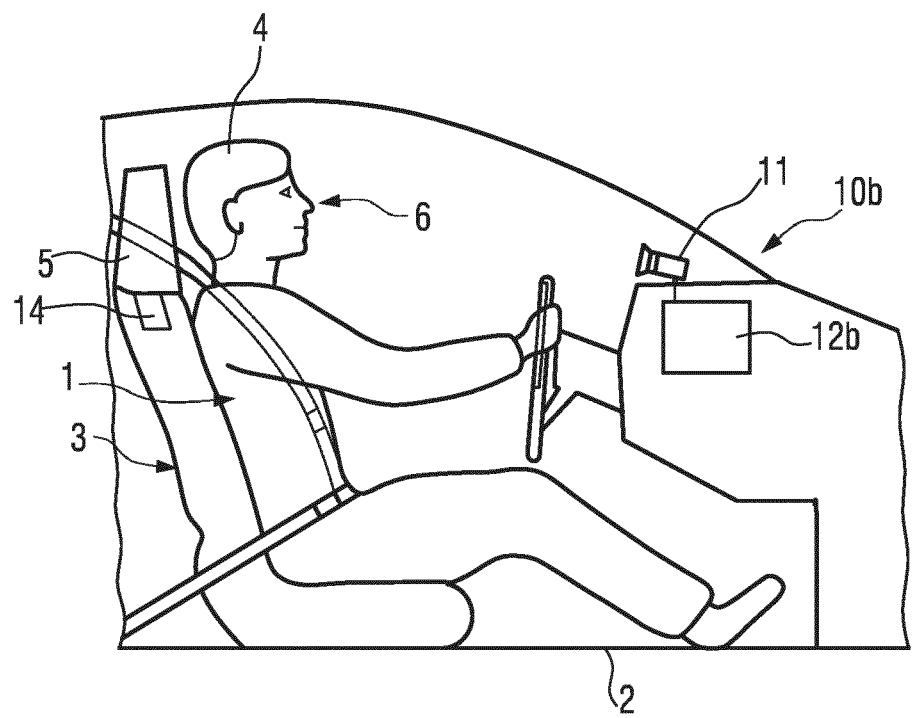
FIG. 4 shows a schematic diagram of a third embodiment of a system and a device according to the present invention.
Figure 4B:
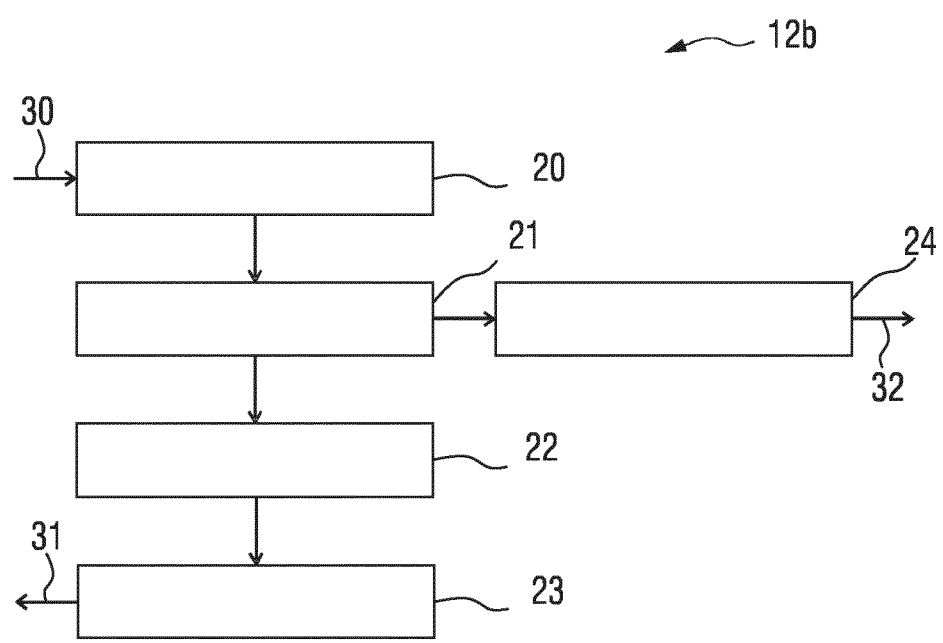

Another embodiment of the system and device according to the present invention is illustrated in FIG. 4, wherein FIG. 4A illustrates the system 10b in the exemplary use scenario used for illustration in FIG. 1 and FIG. 4B shows a schematic diagram of the corresponding device 12b. The system 10b further comprises an actuator 14 for adjusting the position of the support, i.e. the head-rest 5 in this use scenario, to get in contact with body part of interest of the person, i.e. the person's head 4 in this use scenario, based on an support control signal 32. The actuator 14 may be an electric motor integrated into the seat 3, e.g. the backrest 7 and/or the head-rest 5. The support control signal 32 is generated by an support control unit 24 of the device 12b and provided to the actuator 14 in a wireless or wired manner (e.g. via the on-board network of the car 2). It is generally configured to control the position of the support (the head-rest 5) to get in contact with said body part (the head 4) of the person 1 if it has been determined that said body part of the person is not in contact with the support and a vital sign of the person shall be determined.

Thus, e.g. in a smart car, the position of the head-rest can be adjusted electronically and automatically in a smart manner. The head-rest can thus be activated automatically and brought in contact with the driver's head when e.g. the heart rate measurements are initiated. In terms of safety it is preferable that the head is on the head-rest all the time during driving so from this perspective this functionality of the seat is advantageous.

Figure 5A:
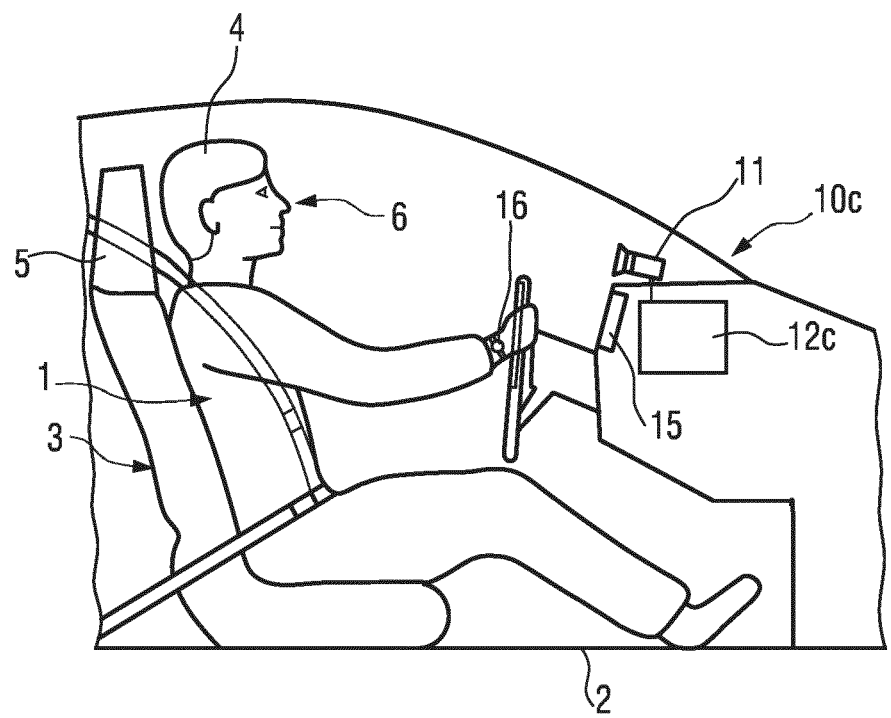
FIG. 5 shows a schematic diagram of a fourth embodiment of a system and a device according to the present invention.
Figure 5B:
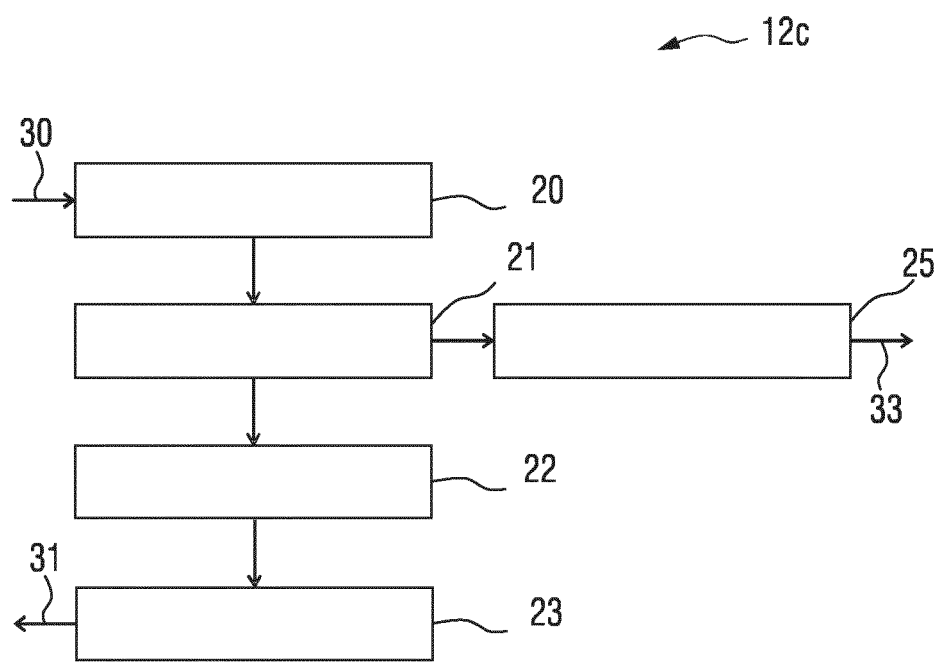

Another embodiment of the system and device according to the present invention is illustrated in FIG. 5, wherein FIG. 5A illustrates the system 10c in the exemplary use scenario used for illustration in FIG. 1 and FIG. 5B shows a schematic diagram of the corresponding device 12c. The system 10c further comprises a user interface 15 (e.g. a display and/or loudspeaker, for instance of the navigation system in a car) for issuing a user instruction 33 instructing the person to move said body part (the head 4 in this use scenario) to get in contract with the support (the head-rest 5 in this use scenario). The user instruction 33 is generated by a user instruction generator 25 and is provided to the user interface 15 in a wireless or wired manner (e.g. via the on-board network of the car 2). The instruction can also be provided via a haptic interface, for example inserted in driver's seat or driving wheel. It is generally configured to instruct the person 1 to move said body part to get in contract with the support if it has been determined that said body part of the person is not in contact with the support and a vital sign of the person shall be determined.

Hence, for certain conditions when e.g. heart rate measurements are necessary or shall be made, the driver can be instructed to place his head on the head-rest. For example, upon activation of the system such an instruction can be displayed. It can then also be checked by use of the information determined by the body part position determining unit 21 if the driver followed the instruction or not so that the instruction can be repeated if the driver did not follow it.

Further, in this embodiment an exemplary wearable sensor 16 (in this embodiment a heart rate sensor worn at the wrist) may be provided (in addition or alternative to the imaging unit 11) for obtaining a wearable sensor signal representing the vital sign related signal. The wearable sensor 16 may generally be any sensor that can be mounted at the patient's body (e.g. like a wrist watch using a wristband, like a body sensor using a belt, like a finger clip using a clip mechanism, e-skin (epidermal electronics), etc.). Exemplary wearable sensors include a heart rate sensor, a respiration sensor, an SpO2 sensor, an accelerometer, a motion sensor, or any other sensor that can be worn at the person's body to acquire a wearable sensor signal, from which a vital sign of the person can be derived or which directly represents a vital sign.

Hence, in this embodiment of the system use is made of the measurements of one (or more) wearable sensor(s) in calculating the reliability of the calculated output. For example, if the person is wearing a wearable device or sensor(s) that is able to measure heart rate, the heart rate signals or values measured by the wearable sensor(s) can be used as an additional (or alternative) input 30 to the proposed device 12c and can be taken into account. For example, a calculated HR output can be labeled as "true" (or "reliable") only if head is resting on headrest, the stricter quality requirements are met, and camera HR output matches the output generated by the wearable sensor(s).

It has been found that vital sign calculations can be done more reliably during night due to limited effect of lighting. Based on this, the quality metric calculation parameters can be relaxed (this "relaxation" can happen in different ways, meaning that the relaxed quality metric when the head is on headrest can be different than the relaxed quality metric calculation parameters in night driving conditions), or the vital sign band (explained above) based on earlier "reliable" values can be defined and used when night conditions are detected or when limited lighting changes are detected. Hence, in another preferred embodiment said quality metric setting unit 12 is configured to additionally use, for setting the quality metric, one or more of the illumination level, light intensity variations, motion of the person, kind and/or parameter of an algorithm for vital sign derivation. Preferably, said quality metric setting unit 12 is configured to additionally use the lighting conditions in the setting of the quality metric. Lighting changes or night conditions may be detected using the acquired images of the imaging unit 11 or using in-car sensors, assuming that car system and vital sign measurement unit are connected and communicating.

The latter embodiments are based on the recognition that a number of artifacts predominantly appear and that the processing of the image data typical comprises a number of processing stages. The total quality metric may therefore be constructed as a combination from several metrics derived from the various parts of the processing chain.

In particular the following sources for artifacts are given: low illumination levels, light intensity variations induced by motion or illuminating sources, and algorithmic choices to resolve particular issues. The quality metric may therefore be constructed—in addition to the above described contact signal—from a measure for sufficient illumination (a sufficiently high signal level relative to the quantization noise), a measure reflecting the success of motion artifact removal, and a measure for sensitivity to the algorithmic choices.

Two or more of these metrics may be combined into the single quality metric, which may be used to control (part of the) operation of the system. Examples are the following. If the current estimate is found to be below a threshold, no value is returned to the user. Alternatively and in view of the fact that physiological variables are often only relatively slowly changing, an older reliable value may be displayed. Yet alternatively, both rules may be combined. Alternatively, the quality metric can be presented to the user. For instance, a traffic (or indicator) light inspired color code can be used, i.e., displaying the physiological value in a green color when considered reliable according to the quality metric, in red when considered unreliable, and orange when uncertain about the reliability, or a number indicating the quality. Both functionalities (control and display) can be combined into the system.

According to such an embodiment a stream of images is used to determine the quantity of interest. One or more internal signals are being picked up to calculate the quality measure. This quality measure is used either to steer the processing and/or create an additional output. As discussed above, vital sign related signal(s) from different sources can be used, including images acquired by an imaging and wearable sensor signals acquired by one or more wearable sensor(s) and can be also included in this calculation.

The processing may comprise a video pre-processing stage where the region of interest is defined and a motion compensation unit is active, resulting in a sequence of stabilized images within a bounded region (or set of regions). The next processing stage may be the core processing where the information in the region of interest and different (color or infrared) channels is combined into a single time-varying signal reflecting the physiological variable of interest (e.g. a blood pulse or respiration signal). A post-processing may be used to extract the feature of interest from this signal, e.g., the heart rate or the respiration rate.

A first metric may look at the signal level of an image (also called frame) and, especially within the region of interest, determine a histogram of the levels (per color or averaged). From these data, possibly combined over different frames, a measure of the illumination level may be obtained. Since estimates of the quantization noise (number of bits) and camera noise (defined by hardware) are known or fixed, the mean, median or other statistical measures of the histogram effectively may be used to define a signal-to-noise ratio. This information is readily available in the pre-processing. Signal to noise ratio can be incorporated in the quality metric parameter calculations, and therefore in the selection of the type of quality metric to be used.

For a second metric several metrics are feasible. In one example, motion compensation may be used to stabilize images. The difficulty of this processing and the errors in the processing are typically directly related to the amount of motion. Therefore the amount of motion in the image in itself can be used as an indicator for the quality of the motion reduction step. This metric is readily available in the pre-processing as a mean displacement factor (which information can be used a part of the quality metric, or to select what type of quality metric to use) or largest displacement vector (within the region of interest).

Having a sequence of motion-compensated images, local or average variance over time of the signals can be looked at. In case of motion compensation and heart rate estimation from skin, a certain signal strength of the blood pulse induced variation is expected (relative to the average signal). If the actually measured variation is much larger (or much smaller) than that expected (from physiology and/or from experience of still images) then the motion induced lighting artifacts are probably insufficiently compensated (or overcompensated). Therefore, a reliability metric can be defined based on signal strength in the motion-compensated images based on information in the (input of the) second processing. Mostly, (relative) signal strengths are typically measures already available within the core processing.

A third metric can take on several variants as well. For almost each building block, alternative implementations are known. E.g., many different motion compensation algorithms are known, many face segmentation have been published, remote PPG estimation core algorithms are available in various variants, and various post-processing algorithms (e.g., frequency estimation in case of respiration or heart rate output) exist. These algorithms have been designed with different points-of-view in mind and typically have (slightly) different optimal operating points. Consistency of the output over different algorithms can therefore be advantageously used as an indicator of simplicity of the condition in which the system is operating. From a practical point of view, some parts of the system are costly to realize for the purpose of the quality metric. For example, a motion compensation unit is a unit requiring quite some processing power. On top of this, the quality metrics for addressing the correctness of this output are already in place. Therefore, from a practical point of view, a quality metric based upon consistency between results stemming from various options of algorithms is more logically situated in the post-processing and core processing.

As an example, a heart rate is the desired output and the post-processing delivers a time-domain signal from which the heart rate has to be determined. Typically, the signal of interest is still weak. Standard methods of estimating the frequency include intermediate representation like an auto-correlation function (ACF) or a frequency representation like a short-time Fourier transform or a power spectral density function. The ACF can be used to determine a lag at which a repetition occurs. The inverse of the lag is proportional to the desired frequency. Due to the weakness of the signal, the determination of the local peaks in the ACF may be difficult, and on top of that, is prone to errors like frequency halving of the fundamental frequency. Alternatively, peaks in the short-time Fourier transform or a power spectral density function may be used as estimates for the desired output. Again, the peaks may be difficult to identify due to the weakness of the signal and frequency doubling can easily occur. If the outputs of both approaches are (almost) equal, this can be considered as an indication of a robustness of the estimate. If both outputs are significantly different, this raises questions about the reliability of either.

In another example, each of the three processing steps explained above in the normal processing feeds information to the quality metric setting. This includes the data stream from the first processing to the quality metric setting and may for instance be statistical information regarding the illumination levels per frame or the frame-to-frame displacement signal(s) as indicators of motion. This further includes the data stream from the core processing to the quality metric setting and may be the expected (relative) variance of signals as discussed before. Still further, this includes the data stream from the post-processing to the quality metric setting and may for instance be outputs generated by different algorithms. These data streams are processed in the quality metric setting based on heuristic or experimentally obtained rules to determine a single quality or reliability measure. This measure can be fed back as a control signal to the different processing steps, or can be fed to a display or storage unit to augment the output of the normal processing chain.

The present invention is not only applicable in the above described use scenario of a driver in a car and the detection of contact of the driver's head with the head-rest of the car's seat. Other use scenarios may be related with other persons (e.g. the driver of a train, truck or bus, a pilot, a patient, etc.), other body parts (e.g. are, hand, leg, foot, chest, torso, etc.) and/or other supports (e.g. arm-rest, back-rest, footrest, seating or lying area, etc.). For instance, the body part position determining unit 21 may be configured to determine if the person's arm and/or hand is in contact with an arm-rest, the person's torso is in contact with a back-rest, the person's leg is in contact with a seating or lying area and/or the person's foot is in contact with a footrest.

Generally, vital signs measurements (e.g. blood pulse and respiration signals) are meaningful indicators in a clinical context. One employment is the use of these signals for synchronization or trigger purposes in scanners in order to have scans reflecting a consistent state of the person. This implies that scanning operations are controlled by the measured vital signs. Such control should only be given if the quality of control signal is sufficiently guaranteed. Therefore, a quality metric based on the extent the observed body part (e.g. the arm) is supported by a rigid structure (e.g. bed of a scanner) or, in other words, the degree of movement of the observed body part is reduced by a proper support is information of appreciable value.

Figure 6:
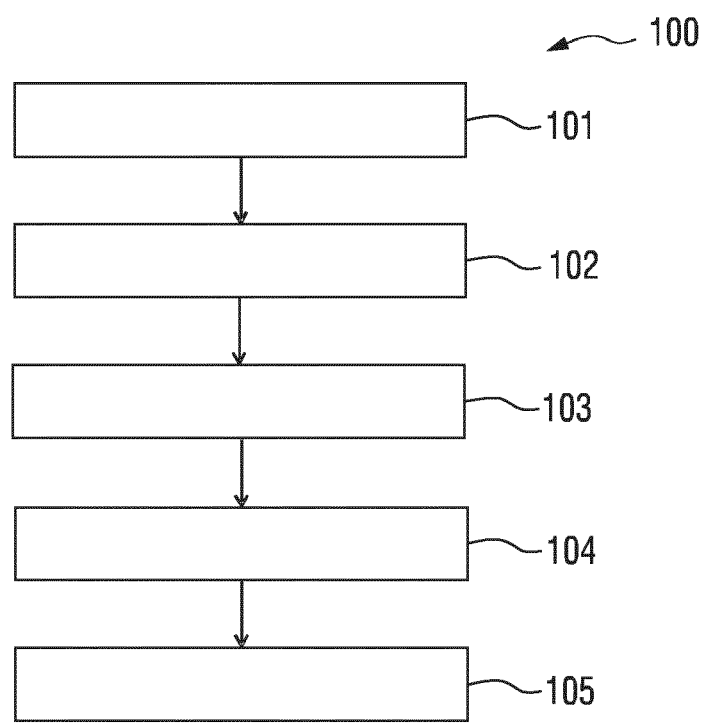
FIG. 6 shows a flowchart of an embodiment of a method according to the present invention.

FIG. 6 shows a flowchart of an embodiment of a method 100 according to the present invention. In a first step 101 a temporal sequence of images of at least a body part of the person, from which a vital sign can be derived, is obtained. In a second step 102 it is determined if said body part of the person is in contact with a support or not. In a third step 103 a contact signal indicating if said body part is in contact with the support or not is generated. In a fourth step, based on said contact signal, a quality metric is set for use in the determination of a vital sign of the person. In a fifth step 105 a vital sign is derived from the obtained sequence of images, wherein the set quality metric is used in the derivation of the vital sign and/or in a judgment of the reliability of a derived vital, in particular in a judgment if and/or to which extent a derived vital sign is reliable.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable non-transitory medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A device for determining a vital sign of a person, the device comprising:
   an input unit that determines a vital sign related signal of at least a body part of the person, from which a vital sign can be derived,
   a body part position determining unit that determines whether the body part of the person is in contact with a support and generates a contact signal indicating whether the body part is in contact with the support, wherein the support is configured to support the body part when the body part is in contact with the support, wherein the contact signal is independent of the vital sign related signal,
   a quality metric setting unit that sets, based on the contact signal, a quality metric for use in a determination of the vital sign of the person, and
   a vital sign deriving unit that derives the vital sign from the obtained vital sign related signal,
      wherein one or more parameters used in the derivation of the vital sign from the obtained vital sign related signal are dependent upon the quality metric.

2. The device of claim 1, wherein the quality metric setting unit is configured to additionally use, for setting the quality metric, one or more of an illumination level, light intensity variations, motion of the person, motion of the body part, motion of the support, motion of the body part relative to the support, kind and/or parameter of an algorithm for vital sign derivation.

3. The device of claim 1, wherein the input unit is configured to obtain, as one or more vital sign related signals, a temporal sequence of images of at least one body part of the person acquired by an imaging unit.

4. The device of claim 3,
   wherein the sequence of images includes a temporal sequence of images of at least the person's face, hand, arm, torso, leg, or foot and
   wherein the body part position determining unit is configured to determine if the person's head is in contact with a headrest, the person's arm and/or hand is in contact with an arm-rest, the person's torso is in contact with a back-rest, the person's leg is in contact with a seating or lying area and/or the person's foot is in contact with a footrest.

5. The device of claim 1,
   wherein the body part position determining unit receives a detection signal from an object sensor in or at the support, wherein the object sensor is configured to detect contact of a person's body part with the support and generates the contact signal from the detection signal.

6. The device of claim 1, wherein the vital sign deriving unit is configured to label vital signs derived when the body part of the person is determined to be in contact with the support as reliable.

7. The device of claim 1, wherein the vital sign deriving unit:
determines whether the vital sign derived within a predetermined time period after a prior vital sign labeled as reliable has been derived deviates from the prior vital sign by more than a predetermined percentage, and
labels the vital sign deviating by less than the predetermined percentage as reliable.

8. The device of claim 1, further comprising an object control unit that generates an object control signal for controlling a position of the support to contact the body part of the person, if it has been determined that the body part of the person is not in contact with the support.

9. The device of claim 1, further comprising a user instruction generator that generates a user instruction instructing the person to move the body part to contact the support, if it has been determined that the body part of the person is not in contact with the support.

10. A system for determining a vital sign of a person, the system comprising:
a vital sign related signal acquisition unit for acquiring a vital sign related signal of at least a body part of the person, from which a vital sign can be derived, and
a device of claim 1 for determining a vital sign of the person based on the acquired vital sign related signal.

11. The system of claim 10, further comprising one or more of
an object sensor arranged in or at a support for detecting contact of the body part of the person with the support and for generating a detection signal indicating if the body part of the person is in contact with the support,
an actuator for adjusting a position of the support to get in contact with the body part of the person based on an object control signal and
a user interface for issuing a user instruction instructing the person to move the body part to get in contact with the support.

12. The device of claim 1, wherein the vital sign related signal is received by the input unit from a wearable sensor.

13. The device of claim 1, wherein the body part position determining unit determines whether the body part of the person is in contact with the support by analyzing a sequence of images of the person, in particular to detect a position, movement and/or orientation of the body part with respect to the support in the obtained sequence of images.

14. The device of claim 1, wherein the quality metric setting unit is configured to additionally use lighting conditions in the setting of the quality metric.

15. A device for determining a vital sign of a person, the device comprising:
an input unit that determines a vital sign related signal of at least a body part of the person, from which a vital sign can be derived,
a body part position determining unit that determines whether the body part of the person is in contact with a support and generates a contact signal indicating whether the body part is in contact with the support, wherein the support is configured to support the body part when the body part is in contact with the support,
a quality metric setting unit that sets, based on the contact signal, a quality metric for use in a determination of the vital sign of the person, and
a vital sign deriving unit that derives the vital sign from the obtained vital sign related signal, wherein the set quality metric is used in the derivation of the vital sign and/or in a judgment of the reliability of a derived vital sign,
wherein the body part position determining unit determines whether the body part of the person is in contact with the support by analyzing a sequence of images representing the vital sign related signal, in particular to detect a position, movement and/or orientation of the body part with respect to the support in the obtained sequence of images.

16. The device of claim 15,
wherein the sequence of images includes a temporal sequence of images of at least the person's face, hand, arm, torso, leg, or foot and
wherein the body part position determining unit is configured to determine if the person's head is in contact with a headrest, the person's arm and/or hand is in contact with an arm-rest, the person's torso is in contact with a back-rest, the person's leg is in contact with a seating or lying area and/or the person's foot is in contact with a footrest.

17. A device for determining a vital sign of a person, the device comprising:
an input unit that determines a vital sign related signal of at least a body part of the person, from which a vital sign can be derived,
a body part position determining unit that determines whether the body part of the person is in contact with a support and generates a contact signal indicating whether the body part is in contact with the support, wherein the support is configured to support the body part when the body part is in contact with the support,
a quality metric setting unit that sets, based on the contact signal, a quality metric for use in a determination of the vital sign of the person, and
a vital sign deriving unit that derives the vital sign from the obtained vital sign related signal, wherein the set quality metric is used in the derivation of the vital sign and/or in a judgment of the reliability of a derived vital sign,
wherein the quality metric setting unit is configured to additionally use lighting conditions in the setting of the quality metric.

18. A method for determining a vital sign of a person, the method comprising:
obtaining a vital sign related signal of at least a body part of the person, from which a vital sign can be derived,
determining if the body part of the person is in contact with a support or not,
generating a contact signal indicating whether the body part is in contact with the support,
wherein the contact signal is independent of the vital sign related signal,
wherein the support is configured to support the body part when the body part is in contact with the support,
setting, based on the contact signal, a quality metric for use in a determination of the vital sign of the person, and
deriving the vital sign from the obtained vital sign related signal, wherein one or more parameters used in deriving the vital sign from the obtained vital sign related signal are dependent upon the quality metric.

19. The method of claim 18, wherein obtaining the vital sign related signal comprises receiving the vital sign related signal from a wearable sensor.

20. The method of claim 18, wherein determining if the body part of the person is in contact with the support by analyzing a sequence of images of the person, in particular to detect a position, movement and/or orientation of the body part with respect to the support in the obtained sequence of images.

21. The method of claim 18, further comprising using lighting conditions in the setting of the quality metric.

22. A non-transitory computer readable medium that contains a program that, when executed by a processor, causes the processor to:
 obtain a vital sign related signal of at least a body part of the person, from which a vital sign can be derived,
 determine if the body part of the person is in contact with a support or not,
 generate a contact signal indicating whether the body part is in contact with the support,
  wherein the contact signal is independent of the vital sign related signal,
  wherein the support is configured to support the body part when the body part is in contact with the support,
 set, based on the contact signal, a quality metric for use in a determination of the vital sign of the person, and
 derive the vital sign from the obtained vital sign related signal, wherein one or more parameters used to derive the vital sign from the obtained vital sign related signal are dependent upon the set quality metric.

23. The medium of claim 22, wherein the program causes the processor to receive a detection signal from an object sensor in or at the support,
 wherein the object sensor is configured to detect contact of a person's body part with the support and generates the contact signal from the detection signal.

24. The medium of claim 22, wherein the program causes the processor to:
 determine whether the vital sign derived within a predetermined time period after a prior vital sign labeled as reliable has been derived deviates from the prior vital sign by more than a predetermined percentage, and
 label the vital sign deviating by less than the predetermined percentage as reliable.

25. The medium of claim 22, wherein the program causes the processor to generate an object control signal that controls a position of the support to contact the body part of the person, if it has been determined that the body part of the person is not in contact with the support.

26. The medium of claim 22, wherein the program causes the processor to generate a user instruction instructing the person to move the body part to get in contact with the support, if it has been determined that the body part of the person is not in contact with the support.

27. The medium of claim 22, wherein the program causes the processor to receive the vital sign related signal from a wearable sensor.

28. The medium of claim 22, wherein the program causes the processor to determine whether the body part of the person is in contact with the support by analyzing a sequence of images of the person, in particular to detect a position, movement and/or orientation of the body part with respect to the support in the obtained sequence of images.

29. The medium of claim 22, wherein the program causes the processor to additionally use lighting conditions in the setting of the quality metric.

30. A non-transitory computer readable medium that contains a program that, when executed by a processor, causes the processor to:
 obtain a vital sign related signal of at least a body part of the person, from which a vital sign can be derived,
 determine if the body part of the person is in contact with a support or not,
 generate a contact signal indicating whether the body part is in contact with the support, wherein the support is configured to support the body part when the body part is in contact with the support,
 set, based on the contact signal, a quality metric for use in a determination of the vital sign of the person, and
 derive the vital sign from the obtained vital sign related signal, wherein the set quality metric is used in the derivation of the vital sign and/or in a judgment of the reliability of the derived vital sign,
 wherein the program causes the processor to determine whether the body part of the person is in contact with the support by analyzing a sequence of images representing the vital sign related signal, in particular to detect a position, movement and/or orientation of the body part with respect to the support in the obtained sequence of images.

* * * * *